(12) United States Patent
Arnissolle

(10) Patent No.: US 6,428,519 B1
(45) Date of Patent: Aug. 6, 2002

(54) INJECTION SYRINGE WITH NEEDLE PROJECTING IN THE SYRINGE BODY

(75) Inventor: Yves Arnissolle, Saint Genis Laval (FR)

(73) Assignee: Societe d'Etudes et d'Applications Techniques-S.E.D.A.T., Irigny (FR)

( * ) Notice: Subject to any disclaimer, the term of this patent is extended or adjusted under 35 U.S.C. 154(b) by 0 days.

(21) Appl. No.: 09/331,210

(22) PCT Filed: Dec. 17, 1997

(86) PCT No.: PCT/FR97/02333
§ 371 (c)(1),
(2), (4) Date: Jul. 29, 1999

(87) PCT Pub. No.: WO98/26825
PCT Pub. Date: Jun. 25, 1998

(30) Foreign Application Priority Data

Dec. 17, 1996 (FR) .......................................... 96 15507

(51) Int. Cl.[7] .............................................. A61M 5/24
(52) U.S. Cl. ........................................ 604/200; 604/198
(58) Field of Search ................................ 604/200, 201, 604/202, 203, 204, 205, 206, 187, 218, 221, 222, 110, 192–199

(56) References Cited

U.S. PATENT DOCUMENTS 2,460,039 A   1/1949  Scherer et al.
4,078,565 A * 3/1978  Genese ........................ 128/220
4,643,721 A * 2/1987  Brunet ........................ 604/191
5,370,628 A  12/1994  Allison et al.
5,658,259 A * 8/1997  Pearson et al. ............. 604/232
6,110,147 A * 8/2000  Perouse ....................... 604/198

FOREIGN PATENT DOCUMENTS

FR   2638091   4/1990

* cited by examiner

Primary Examiner—Anhtuan T. Nguyen
Assistant Examiner—Ann Y. Lam
(74) Attorney, Agent, or Firm—Sughrue Mion, PLLC

(57) ABSTRACT

The invention concerns an injection syringe (10) comprising a syringe body (12) bearing an injecting needle (22) and an actuating piston (14) movably mounted in the body (12). The injecting needle (22) extends axially inside the body (12) up to a rear end (22B) on one side of which is initially arranged in the body (12) a transverse wall (90, 96) capable of being perforated. Said transverse wall (90, 96) is movable relative to the needle from an initial position in which the transverse wall (90, 96) is at some distance from the needle (22) to a final position in which the transverse wall (90, 96) is pierced by said needle (22). The syringe comprises rigid means (64) for axially guiding the rear end (22) of the needle when the transverse wall (90, 96) is being pierced.

12 Claims, 3 Drawing Sheets

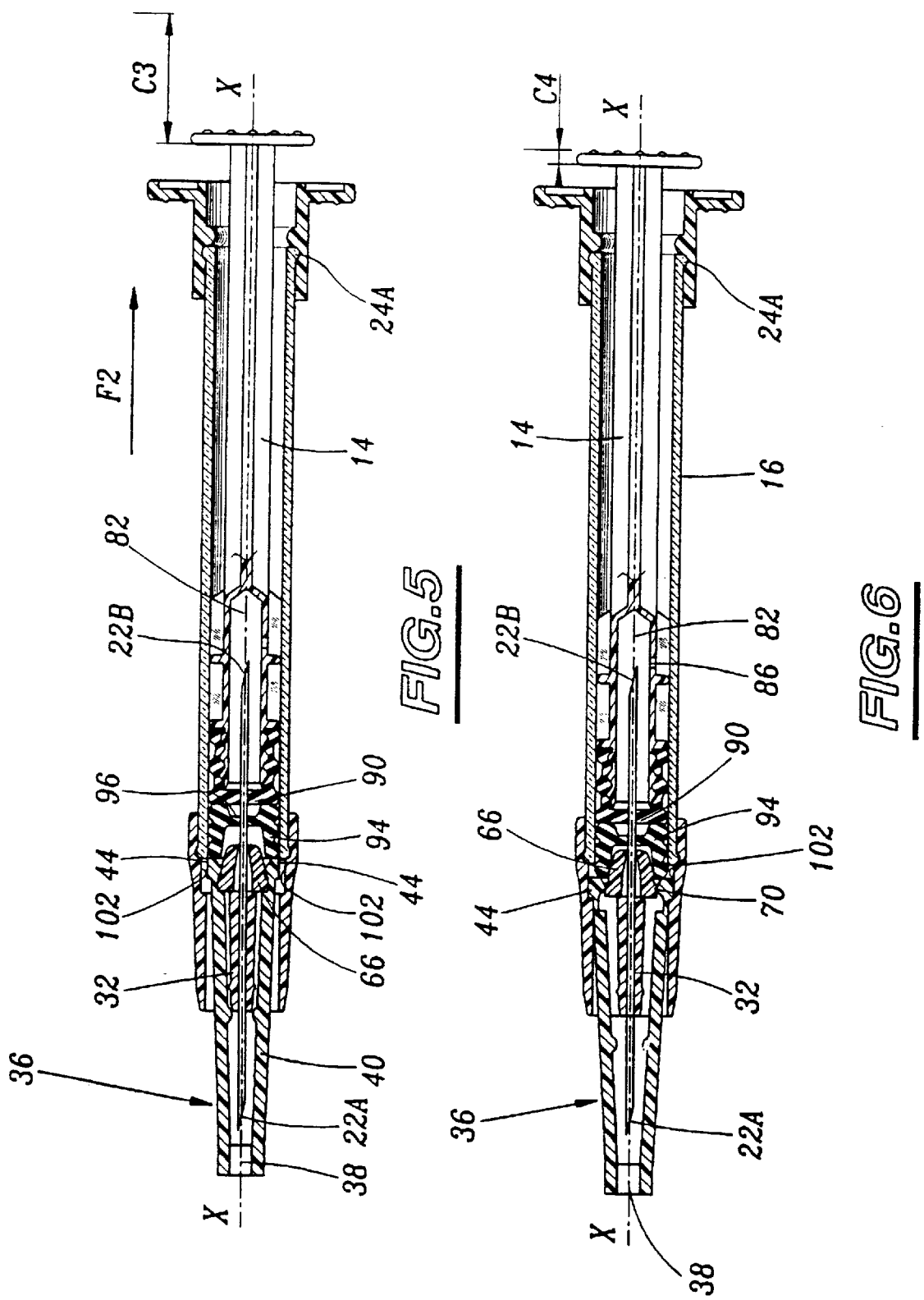

INJECTION SYRINGE WITH NEEDLE PROJECTING IN THE SYRINGE BODY

BACKGROUND OF THE INVENTION

The present invention concerns an injection syringe of the type which includes, on the one hand, an elongate syringe body comprising a tube and a front wall equipped with an injection needle, and, on the other hand, a rear actuating plunger which is mounted so as to be displaceable in the tube, and in which the injection needle continues axially inside the syringe body as far as a rear end, away from which is initially arranged, in the syringe body, at least one perforable transverse wall, the needle and the transverse wall being displaceable relative to one another from an initial position in which the transverse wall is away from the needle as far as a final position in which the transverse wall is pierced by the said needle.

The perforable transverse wall is, for example, carried by the actuating plunger.

In a variant, the transverse wall is for example formed by an intermediate plunger arranged in the syringe body between the rear end of the needle and the actuating plunger. The intermediate plunger then delimits, with the actuating plunger, a housing in which the fluid to be injected is contained.

In the latter case, when the actuating plunger is driven in, the intermediate plunger is perforated by the rear end of the needle in order to allow the fluid to flow through the needle.

If the section of the needle projecting inside the syringe body is long, the intermediate plunger risks being perforated with a slight angular and/or axial offset relative to the axis of the syringe body, because of the low rigidity of the needle.

Under these conditions, at the end of injection, when the actuating plunger comes into contact with the intermediate plunger and pushes it forwards with the view to moving it along the internal section of the needle, the offset existing between the axis of the needle and the axis of the syringe makes it difficult to move the intermediate plunger along the latter and risks leading to obstruction.

SUMMARY OF THE INVENTION

Similar problems are encountered when the transverse wall is carried by the front end of the actuating plunger and constitutes the front face of the latter.

The object of the invention is to make available a solution to the malfunctions of the syringe resulting from an angularly and/or axially offset perforation of the transverse wall by the rear end of the needle.

To this end, the subject of the invention is an injection syringe of the aforementioned type, characterized in that it includes rigid means for axial guiding of the rear end of the needle during the perforation of the transverse wall.

The rigid means for axial guiding of the rear end of the needle hold in position the part of the needle projecting inside the syringe body, so that the latter perforates the transverse wall along the common axis of the needle of the syringe, avoiding the obstruction problems mentioned above.

The subject of the invention is furthermore a needle holder assembly including a wall integral with an injection needle passing through the said wall, as well as a mobile protector of the injection end of the needle, displaceable relative to the needle between a retracted position behind the injection end of the needle and an active protection position in which the front end of the protector is in front of the injection end of the needle, which protector has legs which pass through the said body and extend along the said needle, characterized in that it includes a rigid member for axially guiding the rear end of the needle, which rigid axial guiding member is carried by the free ends of the legs of the protector.

BRIEF DESCRIPTION OF THE DRAWINGS

The invention will be better understood from reading the following description which is given solely by way of example and in which reference is made to the drawings, in which:

FIGS. 3 to 6 are longitudinal cross sections through the syringe in FIG. 1, at different successive stages of use of the syringe.

DETAILED DESCRIPTION OF THE INVENTION

Figure 1:
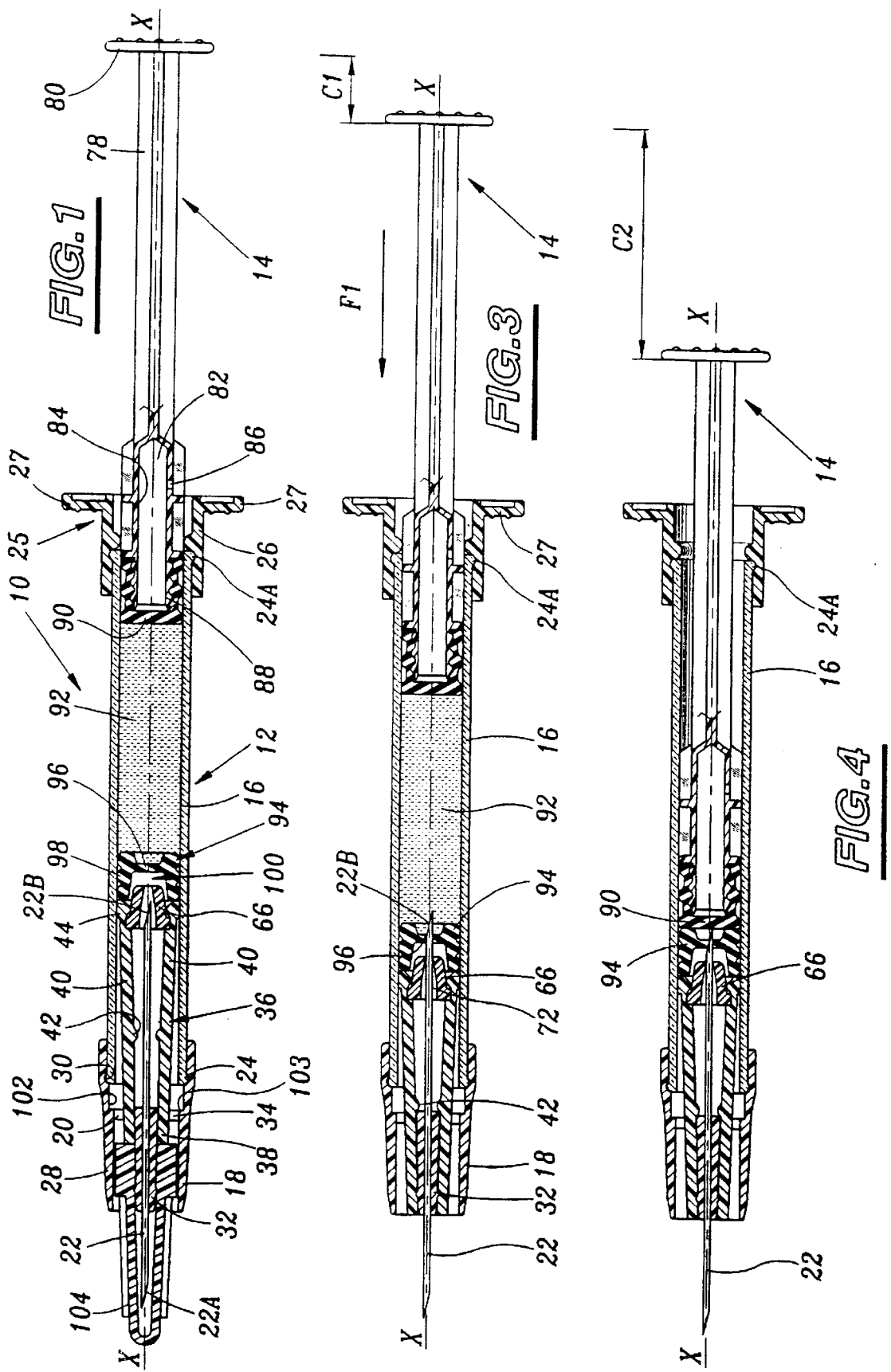
FIG. 1 is a longitudinal cross section through a syringe according to the invention, before use.

The injection syringe 10 represented in FIG. 1, with general form of revolution about axis X—X, is a disposable syringe. It is offered ready for use and already containing a medical fluid to be injected. It essentially includes an elongate syringe body 12 and a rear actuating plunger 14 which is mounted so as to be displaceable inside the body 12.

The syringe body 12 is formed by a tube 16 at the front end of which there is fixed a needle holder 18 which bears a front wall 20 of the syringe body. This front wall 20 is equipped with an injection needle 22 passing through it. The latter includes a front injection end 22A projecting from the body. The needle continues axially inside the body 12 as far as a rear or proximal end 22B. The portion of the needle extending inside the syringe body is longer than the section of the needle projecting outside the syringe body.

The tube 16 is made of glass, for example, and has a circular cross section. Its front end is equipped externally with a peripheral flange 24 for holding the needle holder 18. Likewise, at its rear end, the tube 16 includes externally a peripheral flange 24A. Attached to this rear end there is a grip member 25 which facilitates gripping of the syringe body between the index finger and the middle finger. This grip member 25 includes a sleeve 26 snapped externally onto the end of the tube 16 on the flange 24A, and two diametrically opposite tabs 27 for supporting the fingers.

The needle holder 18 is delimited externally by a sleeve 28. The front wall 20 is made in one piece with the sleeve 28 and extends transversely at an intermediate point of the latter. Formed on the inner wall of the sleeve 28, slightly behind the front wall 20, there is a peripheral groove 30 for receiving the flange 24.

The front wall 20 has an axial stud 32, integral therewith, for fixing the injection needle 22. This stud is directed towards the injection end 22A of the needle and is received inside the space delimited by the sleeve 28.

Three identical openings 34 are made through the front wall 20. They are distributed at uniform angles around the stud 28 on one and the same circular contour and have an arc shape. The figures are longitudinal cross sections of the syringe made on either side of the axis X—X in the middle part of two of the openings 34.

These openings 34 provide for the passage and guiding of a needle protector 36. The latter includes, at the front, a protection ring 38 made of rigid plastic, of which the internal and external diameters are adapted so that the ring 38 lodges in the annular space defined between the stud 32 and the sleeve 18. This ring is continued by three identical legs 40 which are elastically deformable and are spaced angularly at 120°. These legs 40 have, in cross section, a slight curvature corresponding to that of the ring 38 and they have a length substantially equal to the length of that portion of the needle 22 received in the syringe body 12.

Furthermore, each leg 40 includes, over its entire width, a first internal bulge 42 arranged slightly to the rear of the ring 38, and a second external bulge 44 arranged at its free end.

Figures 2, 7:
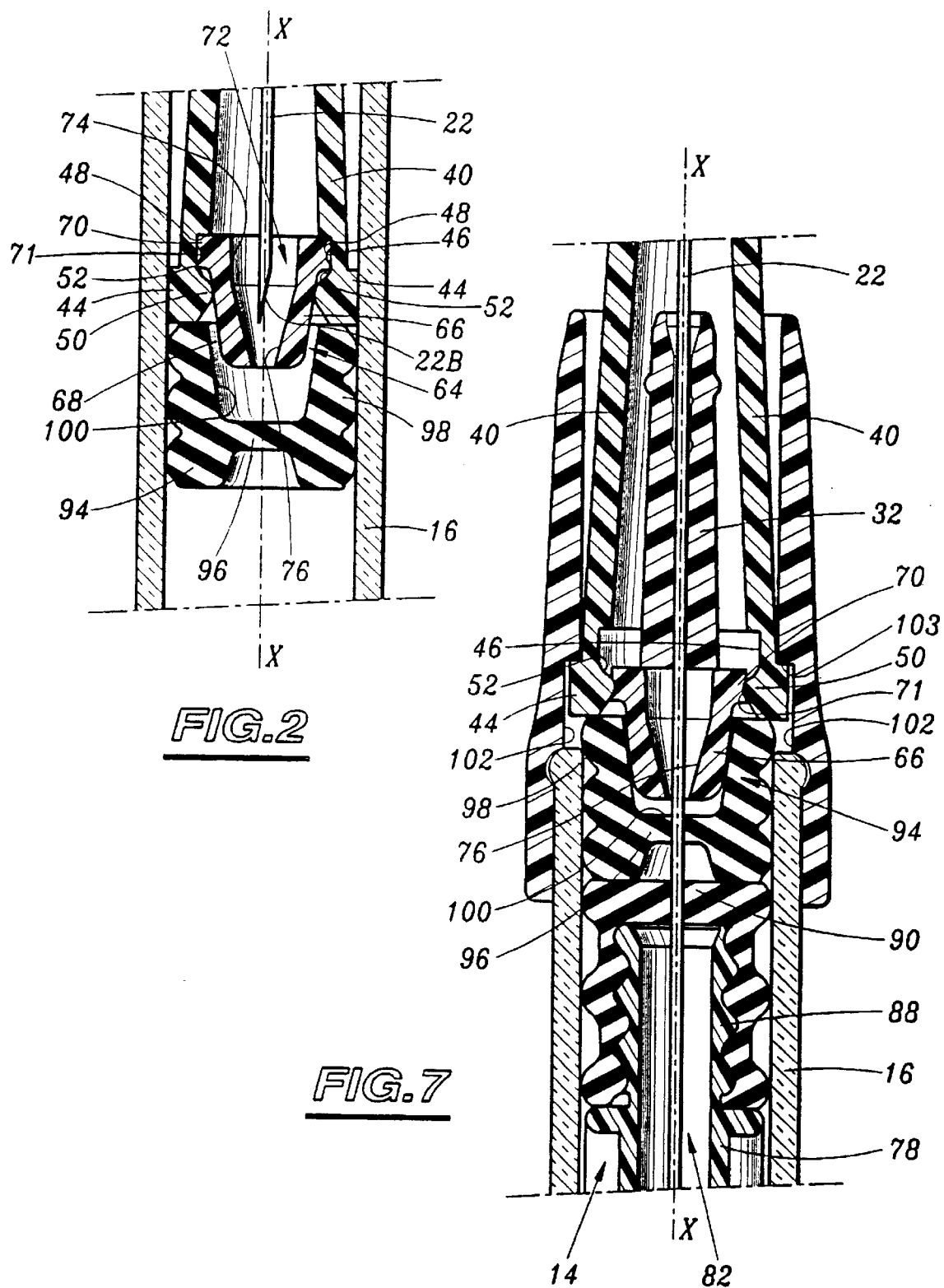
FIG. 2 is a detail, on a larger scale, of the zone surrounding the rear end of the needle of the syringe in FIG. 1.
FIG. 7 is a detail, on a larger scale, of the zone surrounding the front wall of the syringe after completion of the injection.

In addition, as is represented in FIG. 2, the legs 40 include, in the vicinity of their free ends, an internal recess 46 with cylindrical base extending the entire width of each leg. On each leg, this recess 46 is delimited, at the front, by a shoulder 48 formed in the thickness of the leg and, at the rear, by a projection 50 formed in the area of the bulge 44. Each projection 50 carries a cam surface 52 formed by a substantially circular curved surface connecting the rounded summit of the projection 50 to the base of the recess 46.

Means 64 for axial guiding of the rear end 22B of the needle are held between the free ends of the legs 40. These means include a member 66 of revolution held between the legs 40. This member is made of a rigid material, in particular a rigid plastic material. It includes on the outside, to the rear, a truncated lateral wall 68. It is bordered externally, to the front, by a collar 70. The cylindrical lateral surface of the collar 70 is hollowed out, at its centre viewed in the direction of the axis X—X, with a shallow peripheral groove 71. The depth of the groove is in particular less than the height of the bulges 44. Before use of the syringe (FIGS. 1 and 2), the collar 70 is received in the recess 46 and its lateral surface bears on the cylindrical base of the recess 46. The bulges 44 of the legs are then pressed against the inner surface of the tube 16. Thus, the member 66 is held centred along the axis X—X by cooperation with the wall of the body of the syringe.

The member 66 includes an axial passage 72 passing right through it. This passage includes, at the front, a cylindrical portion 74 which is continued by a portion 76 whose cross section decreases progressively towards the rear. This portion 76 is defined by a truncated surface whose cross section, at its narrowest end, is substantially equal to that of the needle 22.

As is represented in FIG. 2, before the syringe is used, the rear end 22 of the needle extends inside the passage 72, so that the end of the needle is completely covered by the member 66.

The rear plunger 14 includes an elongate pusher 78 with a cruciform cross section and has at its rear end a plate 80 for supporting the operator's thumb. At its opposite end there is an axial seat 82 which is open to the front and is used for receiving the rear end 22B of the needle upon completion of injection. This seat 82, of elongate shape along the axis X—X, has a circular cross section. It is delimited by a cylindrical wall 84 equipped with a calibrated vent 86.

The wall 84 has on the outside, at its front end, a helical flange 88 for engaging and fixing a cup-shaped end membrane 90. This membrane closes off the principal front opening of the seat 82 and constitutes a transverse wall adapted to slide in a leaktight manner inside the tube 16.

As is represented in FIG. 1, the fluid to be injected 92 is arranged inside the tube 16 in a space delimited by the membrane 90 of the rear plunger and an intermediate plunger 94. The intermediate plunger 94 includes a perforatable transverse wall 96 surrounded by a lateral sleeve 98 integral therewith and equipped with external peripheral ribs in order to ensure leaktightness of the liquid and the gas between this and the internal lateral wall of the tube 16. The intermediate plunger 94 is initially applied against the end of the needle protector. The wall 96 and the sleeve 98 delimit, to the front, a cup 100 in which is partially received the rear end of the member 66, which projects from the legs 40.

The front end of the tube 16 is fitted in the sleeve 28 and is held there by snap-locking. The peripheral groove 30 being provided slightly to the rear in relation to the transverse wall 20, the latter delimits, with the front end of the tube 16, an annular channel 102 which is arranged immediately to the rear of the wall 20 and whose base is formed by the sleeve 28. The width of the channel 102, measured along the axis X—X, is substantially equal to twice the width of the bulges 44 measured along this same axis. At the front, the channel 102 is delimited by a shoulder 103 formed in the thickness of the sleeve 18. The depth of the hollow space formed by the channel 102 is substantially equal to the height of the projections formed by the bulges 44.

Moreover, a protective cap 104 for the needle 22 is fitted inside the sleeve 28 and covers the injection end 22A of the needle.

The syringe is assembled in the following way.

The needle holder 18 is stuck on the needle 22. The protector 36 is mounted through the front wall by engagement of the legs 40 in the passages 34. It is arranged in such a way that the front protection ring 38 surrounds the stud 32 and the legs 40 extend along the rear part of the needle 22. The member 66 is then put into place in the recess 46 by elastic deformation of the end of the legs 40. The member 66 is held in position by the elasticity of the legs 40 whose free ends tend, as a result of their design, to approach the end 22B of the needle. The front cap 104 is then put into place by being engaged in the sleeve 28.

The needle holder 18, thus equipped with the cap 104 and the member 66, can be manipulated without risk of damage to the ends of the needle, the latter being protected at both ends. In particular, it can be distributed on assembly lines in vibratory bowl feeders.

In parallel with the assembling of the needle holder, the tube 16 is equipped with the grip member 25. It is filled with the fluid 92 arranged between the intermediate plunger 94 and the actuating plunger 14. The needle holder 18 is put into place by being snap-locked onto the front end of the tube 16, as is represented in FIG. 1.

The introduction of the legs 40 into the tube 16, upon assembly of the needle holder on the tube, is easy because the legs 40 together with the member 66 form a single coherent element whose external diameter (diameter measured in the area of the bulges 44) corresponds exactly to the internal diameter of the tube 16.

In order to proceed with the injection, the operator removes the cap 104. In a customary manner, the operator then uses his thumb to exert pressure on the rear plunger 14 in the direction of the arrow F1, pressing on the tabs 27 with index finger and middle finger.

The pressure thus exerted, transmitted by way of the liquid 92 to the intermediate plunger 94, provokes the displacement of the latter, along a travel marked C1, towards the proximal end 22B of the needle. The latter perforates the wall 96 of the intermediate plunger during the movement of the latter. The displacement of the intermediate plunger 94 is accompanied by the forward displacement of the needle protector 36.

During driving, the member 66 is driven forwards by the needle protector 36 in the recess 46 in which it is held. This is because the legs 40 are applied along the bulges 44 on the lateral wall of the tube 16, thereby holding the member 66 in the recess 46.

Moreover, during the movement of the member 66, the wall 16 ensures, by way of the legs 40, that it is centred and axially guided in order to guarantee its displacement strictly along the axis X—X.

During the joint movement of the intermediate plunger 94 and the member 66, the rear end 22B of the needle first comes into contact with the truncated surface 76. The latter ensures, as the displacement of the member 66 proceeds, progressive centring of the end 22B of the needle. It additionally provides axial guiding of the needle. Thus, when the rear end 22B of the needle emerges from the member 66, the portion of the needle arranged inside the body extends strictly along the axis X—X. It is held there by the end of reduced cross section of the passage 72. The rear end 22B of the needle thus perforates the wall 96 while still being held laterally by the member 66 arranged slightly in front on the needle.

In these conditions, the perforation of the intermediate plunger 94 takes place axially and in the central part thereof, thereby guaranteeing easy subsequent displacement of the plunger 94 on the whole inner portion of the needle 22.

The displacement of the intermediate plunger 94 impaled on the needle 22 is stopped at the end of the travel C1 when the bulges 42 come into abutment on the stud 32, as is represented in FIG. 3. For this purpose, the bulges 42 are dimensioned in such a way that the protector 36 is held in its retracted position in FIG. 3 in which the ring 38 extends in the sleeve 18 despite the pressure exerted by the intermediate plunger.

The travel C1 corresponds to the purging of the syringe. In fact, the displacement of the rear plunger 14 while the intermediate plunger 94 is perforated by the needle ensures evacuation of the air contained in the needle and the flow of a small quantity of the fluid 92 through the latter.

After this purge, the injection end 22A of the needle is introduced into the patient's tissue.

The fluid 92 is then injected through the needle 22 under the effect of the pressure on the rear plunger 14 which is driven in along a travel C2 as far as the position represented in FIG. 4. In this position, the bulk of the fluid 92 is injected and the membrane 90 comes into contact with the rear surface of the intermediate plunger 94.

The continued pressure exerted by the operator on the rear plunger 14 then causes disengagement of the bulges 42 by means of elastic deformation of the legs 40. This results in the forward displacement of the protector 36. When the ring 38 comes into contact with the patient's skin, the travel of the protector is stopped, and continued approximation, along a travel C3, of the thumb pressing on the plate 80 and of the other fingers held against the tabs 27, causes the syringe body 12 to reverse in the direction of the arrow F2 (FIG. 5).

It will be appreciated that the reverse movement of the body 12 causes extraction of the injection needle 22 from the patient's body.

It is also possible, by simply pulling on the syringe body, to extract the needle from the patient's tissue while the syringe is in the position represented in FIG. 4. The driving of the rear plunger 14 into the syringe body is in this case continued with the syringe disengaged from any contact with the patient.

Furthermore, the rear end 22B of the needle pierces through the membrane 90 and is received in the seat 82. On account of the presence of the member 66, the perforation of the membrane 90 takes place strictly along the axis X—X.

In the position represented in FIG. 5, the bulges 44 carried externally by the free end of the legs 40 are arranged opposite the annular channel 102. Moreover, in this position, the member 66 lies with its front face abutting on the stud 32 and the front face 20. It is thus immobilized axially.

During the final phase of driving the plunger 14 along a travel C4, the needle protector 36 is displaced forwards under the action of the pressure of the rear plunger 14 transmitted by the intermediate plunger 94 which is still in contact with the free end of the legs 44. For this purpose, the rear end of the member 66 which projects in relation to the legs 40 withdraws into the cup 100, thus allowing the intermediate plunger 94 to slide despite the immobilization of the member 66.

While the member 66 is immobilized, the cam surfaces 52 formed at the rear of the recess 46 cooperate with the collar 70 forming a cam follower in order to space the free ends of the legs apart. As a result of this spacing apart, the bulges 44 are received in the annular channel 102, as is represented on a larger scale in FIG. 7.

In this position, the projections 50 bordering the recess 46 at the rear rest on the lateral surface of the collar 70, thereby ensuring positive retention of the bulges 44 inside the annular channel 102 and positive blocking of the needle protector 36.

Moreover, the projections 50 are received in the peripheral groove 71 of the collar, thereby ensuring axial connection of the member 66 and of the needle protector 36. Thus, even if the needle protector is caused to displace slightly axially (along the length of the annular channel 102), the member 66 is entrained and remains opposite the bulges 44, which permits permanent positive retention of the bulges 44 in the channel 102. Thus, the ends of the legs 40 cannot be released, which guarantees the locking of the needle protector 36 in its active protection position.

In FIGS. 6 and 7, the protector 36 is in the active protection position and extends around the injection end 22A of the needle. The front face of the protection ring 38 is thus situated slightly in front of the end 22A of the injection needle, prohibiting any contact between the latter and an external element and thereby preventing any risk of the operator being contaminated by a stick injury.

It will be appreciated that the bulges 44 engaged in the channel 102 between the shoulder 103 and the end of the tube 16 hold the protector 36 firmly in the protection position, thereby prohibiting any accidental retraction. This hold is in fact guaranteed by the presence of the member 66, whose collar 70 keeps the ends of the legs 40 spaced apart.

The membrane 90 having been perforated by the rear end 22B of the needle, the syringe is rendered unavailable for further use. The reason is that this perforation prohibits the suction effect normally obtained inside the body upon withdrawal of the rear plunger on account of the presence of the vent 86. Likewise, the rear plunger, once perforated, does not allow expulsion, via the injection needle 22, of any liquid re-introduced into the syringe body.

It will be appreciated that in a syringe such as the one described here, the member 66 guarantees a correct perforation of the intermediate plunger 94. This is because the end 22B of the needle, guided by the truncated surface 76, penetrates at the centre of the plunger 96 and along the axis X—X of the syringe.

In the example described, the member 66 is initially arranged around the end 22B. However, the member 66 can be arranged on the needle slightly in front of its rear end, while still correctly exercising its guide function for the rear end of the needle.

Moreover, in the case of a syringe in which the needle holder 18 is equipped with sealing means between the wall 20 and the legs 40, the intermediate plunger 94 is omitted. However, the member 66 is advantageously kept in order to ensure, in the position analogous to that in FIG. 4, perforation of the transverse wall 90 of the rear plunger strictly along the axis X—X of the syringe, thus guaranteeing correct axial penetration of the needle in the seat 82.

In a variant which is not shown, the projecting elements formed by the bulges 44 and the associated complementary recessed element formed by the annular channel 102 are inverted. Thus, the legs include recesses externally, whilst the syringe body has complementary projections with a view to holding the protector in its active protection position.

In this variant too, the member 66 ensures positive retention of the engagement of the associated projecting and recessed reliefs when the needle protector is in its active protection position.

What is claimed is:

1. An injection syringe (10) including an elongate syringe body (12) comprising a tube (16) and a front wall (20) equipped with an injection needle (22), and a rear actuating plunger (14) which is mounted so as to be displaceable in the tube (16), and in which the injection needle (22) continues axially inside the syringe body (12) as far as a rear end (22B), away from which is initially arranged, in the syringe body (12), at least one perforable transverse wall (90, 96), the needle (22) and the transverse wall (90, 96) being displaceable relative to one another from an initial position in which the transverse wall (90, 96) is away from the needle (22) as far as a final position in which the transverse wall (90, 96) is pierced by the needle (22), the syringe further including a mobile protector (36) of an injection end (22A) of the needle, which is displaceable relative to the body (12) under the effect of driving the actuating plunger (14) into the body (12), between a retracted position in the body behind the injection end (22A) of the needle and an active protection position in which the front end of the protector is in front of the injection end (22A) of the needle, which protector has legs (40) which pass through the syringe body (12) and extend partially in the body (12) along the needle (22), wherein the syringe further includes a rigid member (64) for axially guiding the rear end (22B) of the needle when the transverse wall (90, 96) is being perforated, which rigid axial guiding member (64) is carried by free ends of the legs (40) of the protector.

2. Syringe according to claim 1, characterized in that the said rigid axial guiding member (64) includes a passage (72) for guiding the rear end (22B) of the needle, the cross section of the said passage (72) decreasing over at least a part of its length towards the said transverse wall (90, 96).

3. Syringe according to claim 2, characterized in that the rear end (22B) of the needle is initially arranged in the said passage (72).

4. Syringe according to claim 2, characterized in that the said guiding member (66) includes means (44, 46, 70) for centring the said member relative to the axis (X—X) of the needle (22), which centring means initially co-operate with the internal lateral wall of the syringe body (12) in the vicinity of the rear end (22B) of the needle.

5. Syringe according to claim 4, characterized in that the said guiding member (66) is mounted so as to be displaceable along the needle (22).

6. Syringe according to claim 5, characterized in that the rear end of the needle is completely covered by the said rigid guiding member (64) and is behind it.

7. Syringe according to claim 6 taken, characterized in that the legs (40) include, externally at their free end, projections (44) adapted to be received in a hollow (102) formed in the lateral wall of the body (12) when the protector (36) is in the active protection position, the guiding member (66) being arranged between the legs (40) of the protector and displaceable with it as far as an immobilization position abutting against the syringe body, and in that the legs (40) include cam surfaces (52), co-operating with the guiding member (66) when the latter is immobilized, in order to space apart the ends of the legs (40) by axial displacement of the needle protector (36) during the final phase of driving the actuating plunger (14) into the body (12), the guiding member (66) ensuring positive retention of the projections (44) in the hollow (102).

8. The syringe according to claim 1, characterized in that the protector (36) and the syringe body (12) include associated protecting and recessed reliefs (44, 102) for maintaining the protector (36) in its active protection position, and in that said rigid axial guiding member (64) includes means (66) for positive retention of the engagement of said associated projecting and recessed reliefs (44, 102) when the protector (36) is in its active protection position.

9. Syringe according to claim 1, characterized in that the transverse wall (90) is carried by the actuating plunger (14).

10. Syringe according to claim 1, characterized in that the or a transverse wall (96) is carried by a perforable intermediate plunger (94) arranged between the rear end (22B) of the needle and the actuating plunger (14), the intermediate plunger (94) delimiting, with the actuating plunger (14), a housing for a fluid (92) to be injected.

11. A needle holder assembly including a wall (20) integral with an injection needle (22) passing through the wall (20), and a mobile protector (36) of an injection end (22A) of the needle, displaceable relative to the needle between a retracted position behind the injection end (22A) of the needle and an active protection position in which a front end of the protector (36) is in front of the injection end of the needle, which protector has legs (40) which pass through the wall (20) and extend along the needle (22), wherein the holder further includes a rigid member (64) for axially guiding the rear end of the needle, which rigid axial guiding member (64) is carried by free ends of the legs (40) of the protector.

12. Needle holder assembly according to claim 11, characterized in that the rear end of the needle is completely covered by the said rigid guiding member (64) and is behind it.

* * * * *